United States Patent [19]
Gustavel

[11] Patent Number: 5,348,028
[45] Date of Patent: Sep. 20, 1994

[54] COMPACT MULTI-USE ORAL HYGIENE DEVICE

[76] Inventor: Terry L. Gustavel, 5532 Randolph Dr., Boise, Id. 83709

[21] Appl. No.: 132,049
[22] Filed: Oct. 5, 1993
[51] Int. Cl.5 .......................................... A45D 44/18
[52] U.S. Cl. ................... 132/309; 132/308
[58] Field of Search ............. 132/308, 309, 310, 311, 132/321, 323, 324, 325; 401/123, 124, 125, 191; 15/167.1

[56] References Cited

U.S. PATENT DOCUMENTS

| 710,498 | 10/1902 | McClain | 132/321 |
| 2,640,488 | 6/1953 | Veldota | 132/308 |
| 2,980,119 | 4/1961 | Rebstock | 132/308 |
| 3,847,168 | 11/1974 | Schlegel | 132/309 |
| 4,105,120 | 8/1978 | Bradberry | 206/581 |
| 4,576,190 | 3/1986 | Youssef | 132/89 |
| 4,919,156 | 4/1990 | Gipson | 132/309 |
| 4,957,125 | 9/1990 | Yaneza | 132/309 |

FOREIGN PATENT DOCUMENTS 0191896 1/1923 United Kingdom ............... 132/329

Primary Examiner—Gene Mancene
Assistant Examiner—Frank A. LaViola
Attorney, Agent, or Firm—Albert M. Crowder, Jr.

[57] ABSTRACT

A dental hygiene kit comprises handle and toothbrush sections which may be separated for storing the brush in a compact relation with the handle. The handle includes an internal cavity for storing included dentifrice, a dental pick and dental floss. A removable cover containing air holes is provided to cover the brush bristles for sanitation purposes.

12 Claims, 3 Drawing Sheets

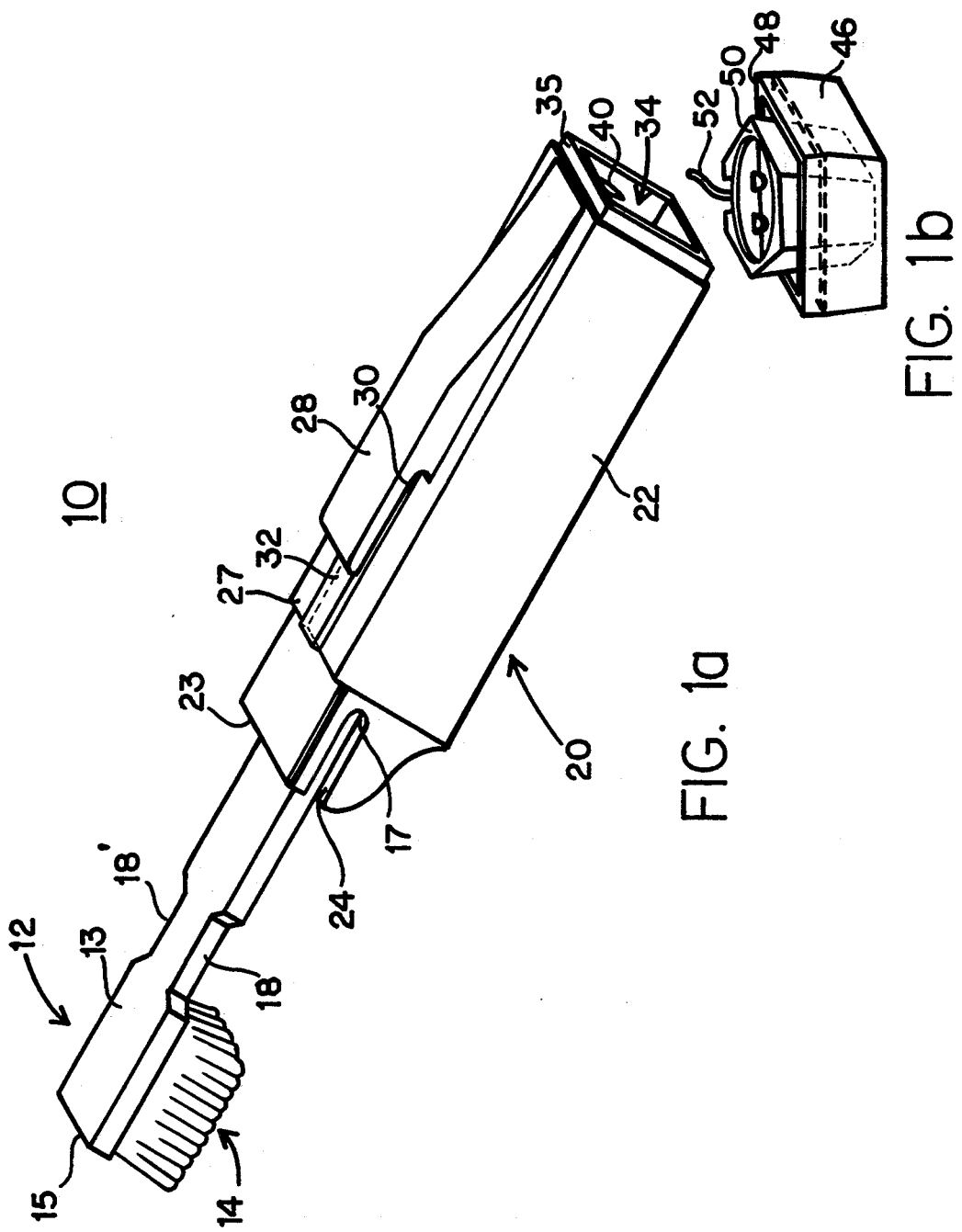

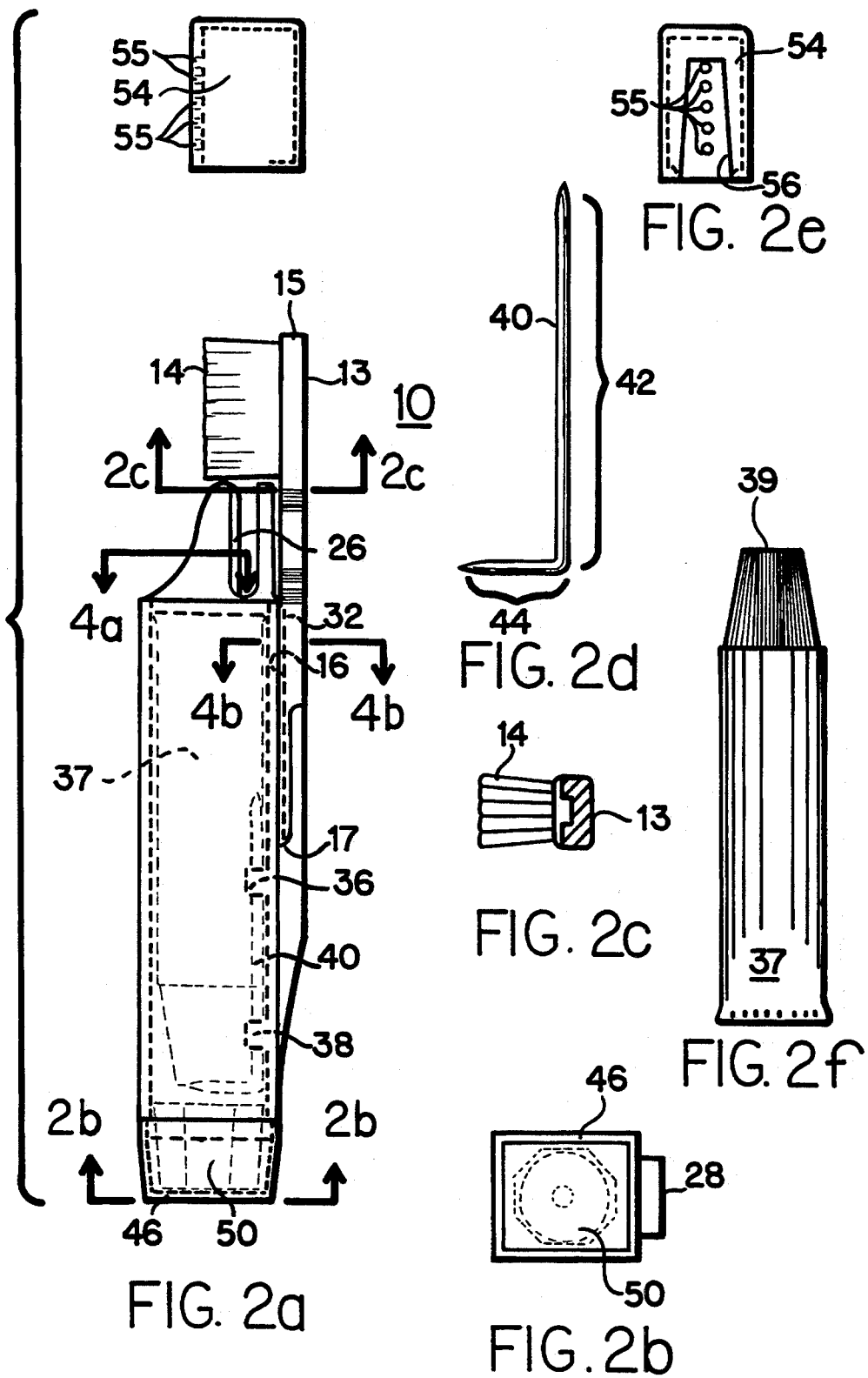

COMPACT MULTI-USE ORAL HYGIENE DEVICE

TECHNICAL FIELD

This invention relates to dental hygiene apparatus, and is more particularly concerned with a reusable, compact, multi-use, breakdown oral hygiene device, having a toothbrush with a covering sheath which can be placed in an operative or a stowed position relative to a handle containing dental floss, toothpaste and a dental pick, all of which components may be replaced as necessary.

BACKGROUND OF THE INVENTION

Personal dental hygiene generally refers to the use of toothbrushes, toothpastes/gels, dental floss, toothpicks and the like. To be effective, these various items must be utilized periodically, in particular, following meals or snacks and regardless of the location. Carrying the various items is awkward and as a result the tendency becomes not to brush or otherwise perform dental hygiene except at very convenient times and places. To overcome this deficiency, various structures have heretofore been proposed which are in the nature of toothbrushes having self-contained supply of dentifrice and generally designed for a single use and subsequent disposal. Other devices, which are reusable, are toothbrushes designed to be folded or otherwise compacted to facilitate carrying in a pocket or purse. To be effective, these require the carrying of toothpaste, floss and dental picks separately.

Additionally, flossing devices have been provided in the prior art which, although small in structure, are designed for a single or perhaps several uses and then disposal. Further, the prior art dental hygiene toothbrushes, which are not particularly small, and flossing devices are not packaged together, creating a tendency not to clutter a pocket or purse carrying the means to provide proper dental hygiene.

SUMMARY OF THE INVENTION

According to the present invention, a multi-function dental hygiene kit is provided. One function is a toothbrush having a brush and a handle such that when not in use, the brush may be detached and positioned against the handle in a stowed position for easier carrying. The brush is a standard brush having bristles attached to a shaft in a manner typical of the prior art. The shaft is designed to either mate into a slot at one end of the handle for use or into a separate slot provided on the side of the handle for storage and compactness. The handle, besides providing a mating slot at one end for the brush portion during use, has an opening at the other end leading into a chamber whereby a supply of a dentifrice and a dental pick, such as a "L" shaped plastic toothpick or the like, may be positioned. Additionally, a cap for covering the chamber is provided which has provision for receiving in a wedged fit a supply of dental floss. The cap has means such as ridges positioned thereon to ensure a sealed fit when placed over the handle's open end, enclosing the chamber.

Clamps built into or otherwise formed on the inside of the chamber allow positioning within the chamber of the plastic toothpick, in the form of a slim cylinder having tapered ends, and which is bent at a 90-degree angle to form a long dimension and a short dimension.

When the brush is positioned on the handle in a stowed position, a cap is provided to cover the brush to provide for sanitation and in such stowed position, the device may be easily carried in a purse or in a pocket and is available for use as needed. Airholes are formed in the cap to facilitate drying of the toothbrush bristles.

Hence, it is an object of the present invention to provide an easily carried dental hygiene device which has associated with it all the features required to provide standard dental hygiene in one single device.

It is still a further object of the present invention to provide a portable device that will permit a complete dental hygiene program to be maintained even when partaking of in-between-meal snacks and at such other times and places where it has heretofore been inconvenient to immediately perform dental hygiene.

BRIEF DESCRIPTION OF THE DRAWINGS

Other objects, features and advantages of the invention, its organization, construction and operation, will be best understood from the following detailed description, taken in conjunction with the accompanying drawings, in which:

FIG. 1(a) is a perspective view of the present invention with the handle end cap removed.

FIG. 1(b) is a perspective view of the end cap of the present invention.

FIG. 2(a) is a side elevation of the present invention showing same in the stowed or travel position with the bristle cap positioned above for clarity.

FIG. 2(b) is an end elevation of the device of FIG. 2(a) taken in the direction 2B—2B'.

FIG. 2(c) is an end elevation of the bristle portion of the present invention taken in the direction 2C—2C'.

FIG. 2(d) is a side elevation of the dental pick of the present invention.

FIG. 2(e) is a back elevation of the bristle cap taken in the direction 2E—2E'.

FIG. 2(f) is a side elevation of a tube of dentifrice dimensioned to fit inside the handle of the present invention.

FIG. 4(a) is an end elevation of the device in FIG. 2a taken in the direction 4a—4a.

DETAILED DESCRIPTION OF THE PREFERRED EMBODIMENTS

Figure 3A:
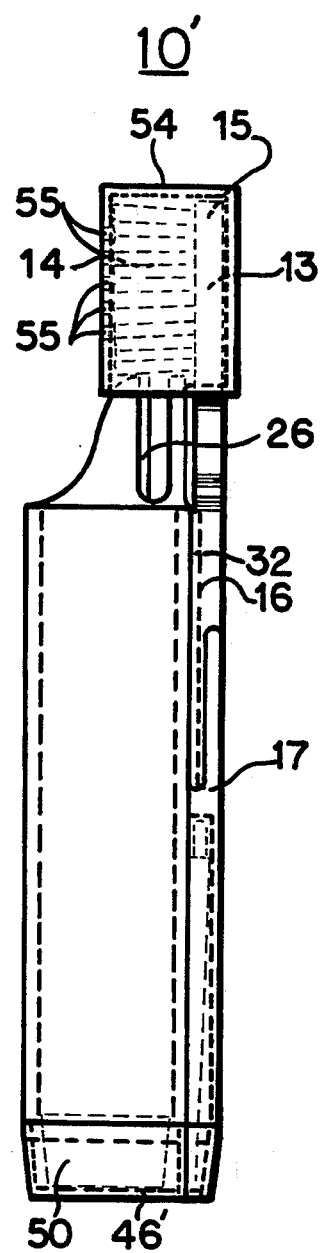
FIG. 3(a) is a side elevation of a different embodiment of the present invention and showing the bristle cap in place.

Referring now to FIGS. 1(a) & (b) and 2(a)-(f) of the drawings, a dental hygiene kit encompassing one embodiment of the present invention is illustrated generally at 10 and comprises two main sections, a brush section 12 and a handle section 20.

The brush section 12 includes a flat shaft 13 having bristles 14 of the type typically utilized in the manufacture of toothbrushes attached to shaft 13 and positioned perpendicular to a surface of shaft 13 proximate to one end 15 thereof and having the opposing end 17 of shaft 13 including a groove 16 (see FIG. 2(a)) formed in the shaft 13 on the same surface to which the bristles 14 are attached for purposes that will be more clearly defined hereafter. The shaft 13 width tapers to a reduced width (shown at 18—18') immediately adjacent to the bristles 14 and extends in such narrowed dimension toward the opposing end 17 for a predetermined distance and thereafter tapers out to resume the original dimension.

The second section 20 of the present embodiment of the invention forms a generally rectangular cross-section hollow handle 22 having at one end 23 a slot 24 situated to receive end 17 of shaft 13 in a snug fit. A ridge 26 (see FIG. 2(a)) is formed on the inside of slot 24 and situated to mate with the groove 16 in shaft 13 of brush section 12. The groove 16 and ridge 26 in mated relation act to provide stability when the dental kit 10 opened or otherwise placed in the extended position for use.

As is readily apparent, The ridge 26 may be formed on the opposing surface of slot 24 if the groove 16 formed in shaft 13 is formed on the side of shaft 13 opposite the side to which bristles 14 are affixed. As the purpose of groove 16 and ridge 26 is to provide stability to shaft 13 when in the extended position, the placement of groove 16 and ridge 26, so long as they can be placed in a mated relation, becomes a matter of choice in manufacturing.

As an integral part of the present invention, handle 22 has formed on one side 27 a raised portion 28 so designed as to form a slot 30 with respect to side 27 and positioned so that slot 30 opens toward end 23 of handle 22. A ridge 32 is formed on side 27 and extends from within slot 30 a predetermined distance toward end 23. The ridge 32 is dimensioned identical to ridge 26 in slot 24 and is also designed to mate with groove 16 in shaft 13 and provide stability for the brush section 12 when placed in the stowed or travel position as shown in particular detail in FIG. 2(a).

The handle 22 defines a cavity 34 intended for use as a receptacle for a small tube, or similar container, 37 and tube cap 39 shown in FIGS. 2(a) & 2(f) containing a quantity of a dentifrice such as toothpaste or dental gel. The interior of cavity 34 is extended, forming a lip 35.

Referring now to FIG. 2(a), there is depicted in cavity 34 two retainers 36, 38 used to permit storing a dental pick such as the "L" shaped toothpick 40, which may be formed of plastic or other suitable material, shown in FIG. 2(d). The dental pick 40 is formed from a small diameter shaft having tapered ends with one end bent at an angle of 90° with respect to the longitudinal axis of the shaft to form a "L" shaped dental pick 40 having a long dimension 42 and a shod dimension 44. Referring also to FIG. 1 (a) and 2(a), pick 40 is shown stowed in retainers 36,38 in cavity 34.

Referring now to FIG. 1(b), there is shown an end cap 46 having a lip 48 formed on the exterior of end cap 46 and so dimensioned a to provide a snug fit with lip 35 when the end cap 46 is positioned with respect to handle 22 so as to cover cavity 34 as shown in FIG. 2(a). Additionally, the interior of end cap 46 is geometrically dimensioned to receive in a tight wedge fit a container 50 such as is well known in commercial use for providing a quantity of dental floss 52. Referring also to FIG. 2(b), there is shown a bottom elevation of dental kit 10 taken in the direction 2B—2B' and showing in hidden view the relation of floss container 50 to the end cap 46.

Now referring to FIG. 2(a) and 2(e)there is shown a brush cover 54 of plastic or a like material and dimensioned to fit over the bristles 14 of brush section 12 when kit 10 is in the stowed position shown in FIG. 2(a). The cover 54 is provided for sanitary purposes and includes a cutout 56 which, when cover 54 is placed over bristles 14 the cutout 56 permits the cover 54 expand, permitting it to slide over shaft 13 until it reaches reduced section 18—18' whereby the expanded cover 54 returns to its original shape, clamping the cover 54 in fixed relation to and covering bristles 14. The opposite effect occurs when removing the cover 54 assisted by the tapir between reduced section 18—18' and the original width of shaft 13. Cover includes air holes 55 formed therein to enhance drying of bristles 14 subsequent to use and storage of the device.

Referring to FIG. 3(a), an alternate embodiment 10' of the present invention is shown to include a modification whereby a second smaller chamber or cavity 60 is formed in raised portion 58 on side 27 and is accessible by removing the end cap 46' which has been dimensioned to accommodate covering both cavity 34 and 60 when attached to handle 20.

Figure 3B:
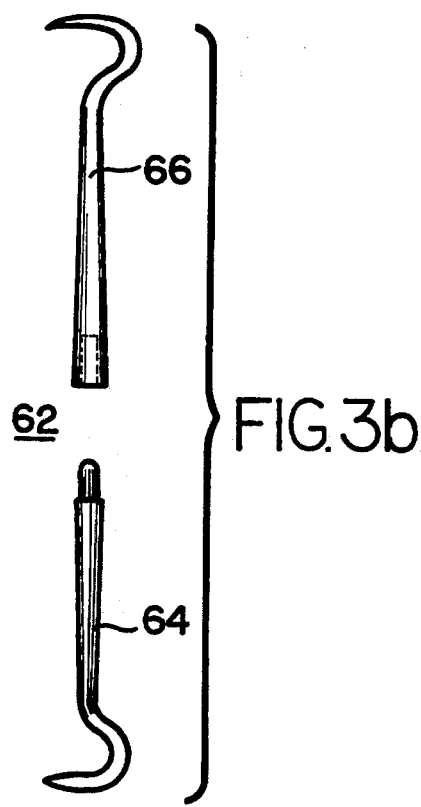
FIG. 3(b) is a second embodiment of the dental pick utilized with the embodiment of the invention shown FIG. 3(a).
Figure 4A:
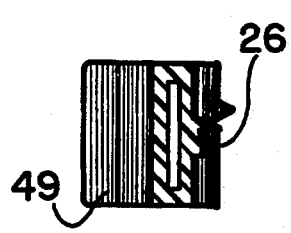
Figure 4B:
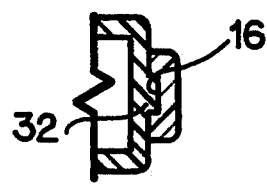
FIG. 4(b) is an end elevation of the device in FIG. 2a taken in the direction 4b—4b.

In FIG. 3(b), there is shown an alternate embodiment of the dental pick 62. Pick 62 is envisioned for use with kit 10' and consists of two shaft sections 64, 66. Each shaft section 64, 66 contains a mating end such as a dowel 72 and a receptacle 74 which, when connected, permit the sections 64,66 to be joined to form a single shaft 62. The opposing ends of each shaft 64,66 includes an arcuate zone ending in a tapered tip 68,70 respectively. Pick 62 is dimensioned such that when sections 64, 66 are uncoupled they will fit in cavity 60 for storage.

In use, it is seen that in the stowed configuration shown in FIG. 2(b) and 3(a), kits 10 and 10' respectively may be readily carried in a pocket or purse until such time as dental hygiene is required. When needed, and referring now to FIG. 1(a) and 2(a) in particular, as the use of kit 10' is essentially the same as for kit 10, shaft 13 is removed from the stowed position of FIG. 2(a) and positioned firmly in slot 24 and cover 54 is removed. Next, end cap 46 is removed and the tube of dentifrice (not shown) is removed and a quantity placed on bristles 14 for use, According to the user's preference, pick 40 may be removed and utilized prior to or after brushing. Also in accord with the user's preference, a quantity of floss 52 may be removed from container 50 for use. The actual sequence of these steps is, as before stated, entirely at the user's preference. After completion of the dental hygiene procedure, the kit 10 may be cleaned and returned to the stowed configuration and replaced in a pocket or purse.

Although particular embodiments of the invention have been described herein, it will be understood that the invention is not limited to the embodiments disclosed and that variations could be made therein without departing from the essential features of the invention and the preferred embodiments are not intended to limit the spirit or scope of the invention as set forth in the appended claims.

I claim:

1. A dental hygiene kit having an operative and a stowed position, comprising:
   a brush section formed from a flat shaft having a longitudinal axis having bristles attached perpendicular to a surface of said shaft and proximate to a first end of said shaft;
   said surface further defining a groove extending from a second end of said shaft opposite said first end and parallel to the longitudinal axis for a predetermined distance;
   an elongated handle defining a rectangular cross-section cavity with an open end and a closed end, said closed end defining a first slot external to said cavity and operative to receive in mated configuration the second end of said brush section and including a first raised portion formed on the interior of said first slot, said first raised portion configured to receive said groove of said brush section so as to place the kit in an operative position;

a second raised portion formed on the surface of said elongated handle, said second raised portion being larger than said first raised portion and said second raised portion defining a second slot having formed therein a third raised portion having the same dimensions as said first raised portion, said second slot and third raised portion operative to receive said second end of said shaft when disengaged from said first slot and placed in said second slot, placing said kit in a stowed position; and an end cap dimensioned to fit snugly over the open end of said handle, enclosing said cavity.

2. The dental hygiene kit of claim 1, wherein said bristles, when the kit is in said stowed position, are positioned over and immediately adjacent said first slot.

3. The dental hygiene kit of claim 2, including an "L" shaped toothpick releasably mounted in a plurality of brackets formed on an interior surface of said cavity.

4. The dental hygiene kit of claim 3, including a bristle cap dimensioned to fit snugly over the bristles when said kit is in said stowed position, said end cap including a plurality of holes therein to facilitate drying when the kit is stowed.

5. The dental hygiene kit of claim 4, further including a container of dental flossing material wherein said end cap is dimensioned to receive, in friction fit, said container of dental flossing material such that when said end cap is positioned over said open end of said cavity said flossing container is positioned in said cavity.

6. The dental hygiene kit of claim 5, further including a tube containing a dentifrice and dimensioned to fit inside said cavity when said toothpick is mounted inside said cavity and said end cap including said flossing material container is positioned over said open end of said cavity.

7. A compact multi-use oral hygiene device having an operative and a stowed position, comprising:

a brush section formed from a flat shaft having a longitudinal axis having bristles attached perpendicular to a surface of said shaft and proximate to a first end of said shaft;

said surface further defining a groove extending from a second end of said shaft opposite said first end and parallel to the longitudinal axis for a predetermined distance;

an elongated handle defining a rectangular cross-section first cavity with an open end and a closed end, said closed end defining a first slot external to said cavity and operative to receive in mated configuration the second end of said brush section and including a first raised portion formed on the interior of said first slot, said first raised portion configured to receive said groove of said brush section so as to place the kit in an operative position;

a second raised portion formed on the surface of said elongated handle, said second raised portion being larger than said first raised portion and said second raised portion defining a smaller second cavity adjacent to and parallel to said first cavity and having an open end proximate to the open end of said first cavity and a closed end defining a second slot having formed therein a third raised portion having the same dimensions as said first raised portion, said second slot and third raised portion operative to receive said second end of said shaft when disengaged from said first slot and placed in said second slot, placing said kit in a stowed position; and an end cap dimensioned to fit snugly over the open ends of said handle and said second raised portion, enclosing said first cavity and said second cavity.

8. The oral hygiene device of claim 7, wherein said bristles, when the kit is in said stowed position, are positioned over and immediately adjacent said first slot.

9. The oral hygiene device of claim 8, including a dental pick having first and second shaft sections, each section having a mating end operative to permit the sections to be joined to form a single shaft, each of said first and second shaft having an opposing end formed in an arcuate shape ending in a tapered tip, wherein said first and second shaft sections, in an unmated configuration, are dimensioned to permit placement of said shaft sections in said second smaller cavity and enclosure by said end cap.

10. The oral hygiene device of claim 9, including a bristle cap dimensioned to be emplaced over and cover said bristles when said kit is in said stowed position, said end cap including a plurality of holes therein to facilitate drying when the kit is stowed.

11. The oral hygiene device of claim 10, further including a container of dental flossing material wherein said end cap is dimensioned to receive, in friction fit, said container of dental flossing material such that when said end cap is positioned over said open ends of said first and second cavities said flossing container is positioned in said first cavity.

12. The oral hygiene device of claim 11, further including a tube containing a dentifrice and dimensioned to fit inside said first cavity when said end cap including said flossing material container is positioned over said open ends of said first and second cavity.

* * * * *